(12) United States Patent
Shinkai

(10) Patent No.: US 6,562,016 B2
(45) Date of Patent: May 13, 2003

(54) WATER ABSORBING PAD, WATER-ABSORBING PRODUCT AND DIAPER USING WATER-ABSORBING PAD, AND METHOD FOR WASHING THE SAME

(75) Inventor: Yoichi Shinkai, Hekinan (JP)

(73) Assignee: Shinkai Co., Ltd., Hekinan (JP)

( * ) Notice: Subject to any disclaimer, the term of this patent is extended or adjusted under 35 U.S.C. 154(b) by 47 days.

(21) Appl. No.: 09/835,574

(22) Filed: Apr. 17, 2001

(65) Prior Publication Data

US 2001/0034510 A1 Oct. 25, 2001

(30) Foreign Application Priority Data

Apr. 21, 2000 (JP) ........................................ 2000-121368
Dec. 28, 2000 (JP) ........................................ 2000-403060

(51) Int. Cl.⁷ ............................ A61F 13/15; A61F 13/20
(52) U.S. Cl. ................... 604/385.01; 604/358; 604/364
(58) Field of Search ............................ 604/384, 385.01, 604/358, 364, 367, 378, 385.03, 385.15

(56) References Cited

U.S. PATENT DOCUMENTS

| 4,573,987 | A | * | 3/1986 | Lamb, Jr. ................... 604/378 |
| 4,923,454 | A | * | 5/1990 | Seymour et al. ............ 604/368 |
| 5,767,168 | A | * | 6/1998 | Dyer et al. .................. 521/149 |

* cited by examiner

*Primary Examiner*—Henry Bennett
*Assistant Examiner*—Alfred Basichas
(74) *Attorney, Agent, or Firm*—Kanesaka & Takeuchi

(57) ABSTRACT

A paper diaper using an water-absorbing polymer is superior in absorbency/water-retaining performance to a cloth diaper, but it has the drawback that it generates garbage and is expensive. An water-absorbing pad is formed by allowing an water-absorbing polymer which is dispersed, dissolved or melted or the crosslinks of which are broken in an electrolytic aqueous solution to be retained by a water soluble material. An water-absorbing product is produced by interposing the water-absorbing pad thus formed between sheets of cloth or other materials. The water-absorbing pad secured within the product is dissolved when washed with an electrolytic aqueous solution, and the product itself is reusable.

29 Claims, 8 Drawing Sheets

WATER ABSORBING PAD, WATER-ABSORBING PRODUCT AND DIAPER USING WATER-ABSORBING PAD, AND METHOD FOR WASHING THE SAME

BACKGROUND OF THE INVENTION

1. Field of the Invention

The present invention relates to an water-absorbing pad whereby to improve the absorbency of an water-absorbing product such as a diaper or a urine-receiving pad; an water-absorbing product using this water-absorbing pad; and to a method for washing a diaper or other water-absorbing products using the water-absorbing pad.

2. Description of the Related Art

Generally, a diaper for infants, the sick, and elderly people is composed of a cloth diaper and a diaper cover which is put thereon as a set. Particularly, in the case of an adult wearer, several cloth diapers (for example, three diapers) are often used in layers thereby to improve the absorbency.

Such diaper has the drawback that the excrement stays between the cloth diaper and the wearer's skin and tends cause skin troubles (diaper rash). In addition, if several layers of cloth diapers are used, the diaper will be uncomfortable to wear, for the cloth diapers or the cloth diapers and the diaper cover are dislocated, etc.

The absorbency of the cloth diaper itself can be raised by weaving a cloth in such a manner that the fibers are slackened as loose as possible so that moisture is held therebetween. However, for example, even if a cloth is woven in the manner as described above, the cloth diaper is still required to be made bigger and heavier thereby to ensure an absorbency sufficient for use by an adult, and a diaper using a set of three cloth diapers each weighing, in a dried condition, as heavy as 220 g or so will be quite heavy.

On the other hand, in recent years, paper diapers improved in water absorption and retaining performance through the use of an water-absorbing polymer have come to be popularly employed. These paper diapers, though light, can ensure a sufficient absorbency and have the advantage that, due to their high water retaining performance, they hardly cause skin troubles.

However, paper diapers are generally expensive, and their being disposable presents the problem of waste.

SUMMARY OF THE INVENTION

Accordingly, an object of the present invention is to provide an water-absorbing pad with which to improve the absorbency and water-retaining capacity of a product such as diapers and make the product reusable by enabling it to be easily washable. Another object of the present invention is to provide an water-absorbing product or diaper using such water-absorbing pad, and a method for washing these products.

For achieving the objects mentioned above, in the present invention, an water-absorbing pad is constituted of an water-absorbing polymer which is dispersed, dissolved or melted in an electrolytic aqueous solution (e.g., a salt solution, a sodium hypochlorite aqueous solution, a calcium chloride aqueous solution) or an water-absorbing polymer crosslinks of which are broken in an electrolytic aqueous solution (e.g., a crosslinked polyacrylate-type resin or crosslinked polystarch acrylate-type resin) retained by, for example, being wrapped up in a water soluble material such as a water soluble sheet.

The water-absorbing pad is interposed between sheets of cloth or other materials for such water-absorbing products as diapers or urine-receiving pads. Since the absorbency and water-retaining capacity of the water-absorbing product are satisfactorily ensured through the use of this water-absorbing pad, a high absorbency is not required of the material of the product and therefore a thin and light-weight material can be used, enabling a reduction in the weight of the product as a whole. In the case of a conventional diaper, it is necessary to wrap one diaper constituting a set of three diapers around the waist of the wearer in order to prevent the leakage of urine or other fluids, but the diaper of the present invention eliminates the necessity for wrapping a cloth diaper around the waist like that, consequently making diaper change easier.

Moreover, through the use of a sheet of such a material as to allow moisture (e.g., urine) to easily permeate from its surface-side to the water-absorbing pad-side but hardly allow the reverse as at least one of the sheets between which the water-absorbing pad is interposed (e.g., the skin-side sheet), the moisture absorbed into the pad is prevented from flowing back, releasing the wearer from unpleasantness or skin troubles.

By washing a used water-absorbing product with an electrolytic aqueous solution such as a salt solution in an ordinary manner with the water-absorbing pad incorporated therein, the water-absorbing pad is dissolved, leaving no garbage behind, which not only enables the water used for washing to be discharged without any special sewage treatment but makes it possible to reuse the water-absorbing product.

Even if the water soluble sheet is dissolved when the water-absorbing pad absorbs water, since the pad has been interposed between the sheets, the risk of the remaining water-absorbing polymer leaking out of the product is low. From the viewpoint of complete dispersion, dissolution or melting, or breaking of the crosslinks of the water-absorbing polymer upon washing, dissolution of the water soluble sheet upon water uptake is rather favorable than not.

Moreover, a set of diaper sheets between which the water-absorbing pad is interposed is made detachable from the diaper cover. Thereby, not only does the resulting diaper become easier to wear because of the set of diaper sheets (and the water-absorbing pad interposed therebetween) integrally attached to the cover, but also in the case where the set of diaper sheets is stained or damaged to uselessness, it is made possible to reuse the diaper cover together with a new set of diaper sheets.

Further, the necessity for adding an electrolytic substance to washing water every time the water-absorbing product is washed can be eliminated by the following measures. That is, by impregnating the water-absorbing pad with an electrolytic substance, by incorporating an electrolytic substance or electrolytic aqueous solution into a glue or adhesive to be used for gluing the water soluble sheet, or by using a detergent containing a suitable amount of an electrolytic substance.

DETAILED DESCRIPTION OF THE PREFERRED EMBODIMENTS

First Embodiment

Figure 1:
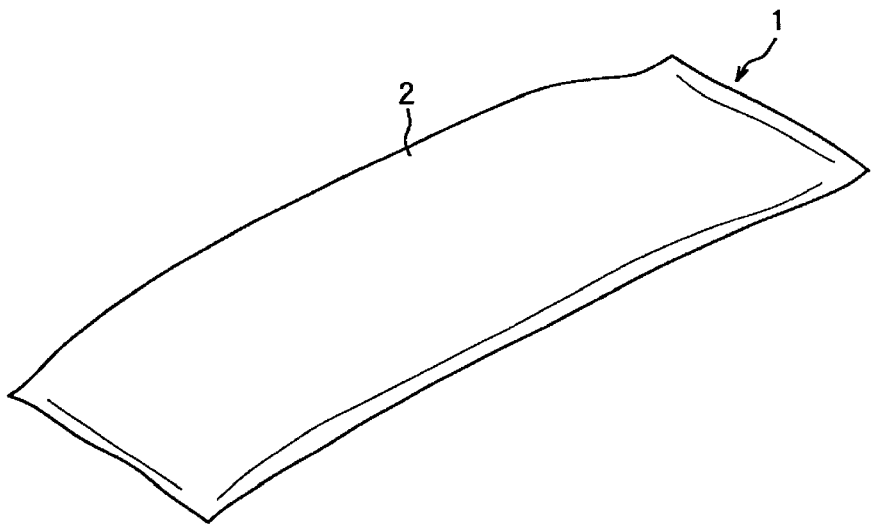
FIG. 1 is a perspective view of the water-absorbing pad which is a first embodiment of the present invention.
Figure 2:
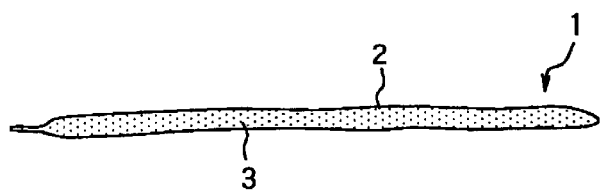
FIG. 2 is a cross-sectional view of the water-absorbing pad.

FIG. 1 and FIG. 2 show an water-absorbing pad which is one embodiment of the present invention. Reference numeral 1 dentoes the above-described water-absorbing pad, and reference numeral 2 denotes water soluble paper (water soluble sheet) constituting the surface of the water-absorbing pad.

The water soluble paper 2, made by for example shaping finely shredded wood pulp in the form of a sheet using starch as a binder, is dissolved in water (and an electrolytic aqueous solution). For example, a piece of water soluble paper 2 is folded in half and glued margin to margin to form an envelope.

The water soluble paper 2 may be one that is produced by any of other methods, and a water soluble non-woven fabric or any of other water soluble sheets can be employed instead of the water soluble paper 2.

Reference numeral 3 denotes a powdered or granular water-absorbing polymer sealed in the water soluble paper 2 in the form an envelope. Employed as the water-absorbing polymer 3 is such a polymer material as to have a high absorbency and water-retaining capacity and be dispersed, dissolved, or melted in an electrolytic aqueous solution, or a polymer material the crosslinks of which are broken in an electrolytic aqueous solution. Examples thereof include crosslinked polyacrylate-type resins and crosslinked polystarch acrylate-type resins.

Alternatively, the water-absorbing pad 1 is produced by, for example, coating or spraying a water soluble adhesive such as starch glue on one side of a water soluble sheets, allowing an water-absorbing polymer to be retained on the adhesive-applied surface by, e.g., spraying, gluing two water soluble sheets together with their polymer-applied sides inside, and drying.

Figure 3:
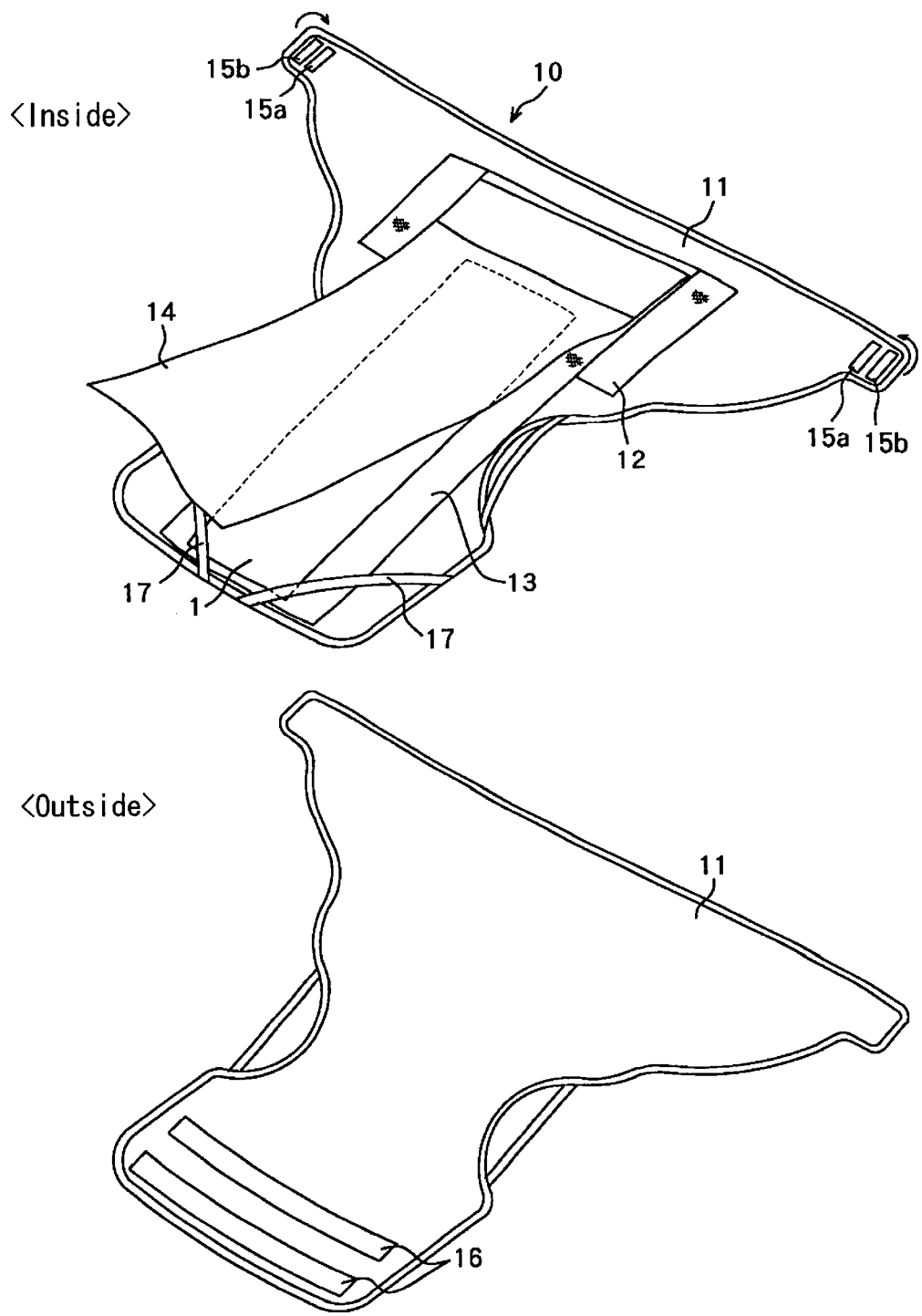
FIG. 3 is a perspective view of a diaper using the water-absorbing pad.
Figure 4:
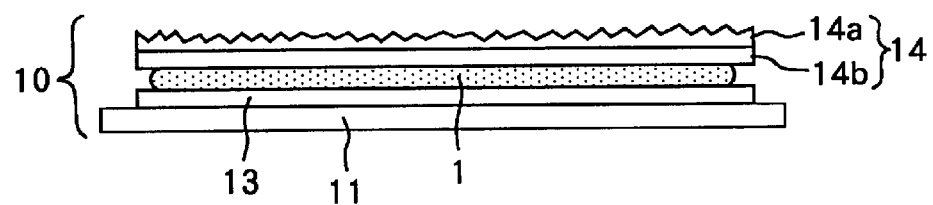
FIG. 4 is a cross-sectional view of the diaper.

The water-absorbing pad 1 thus made is used for a diaper 10 (water-absorbing product) shown in FIG. 3 and FIG. 4.

In these figures, reference numeral 11 denotes a diaper cover, which is made of a high-water-proof synthetic fiber. Examples of such a synthetic fiber include nylon, polyester, polyurethane, polyvinyl chloride and the like.

A Velcro fastener 15b is attached to the inside of each end of the extensions on the left- and right-hand sides of the back body of the diaper cover 11. By pressing the Velcro fasteners 15b against strips of raised cloth 16 attached to the outer central part of the front body of the diaper cover 11, the diaper cover 11 (that is, diaper 10), as a whole, takes on the form of a panty.

On the inside of each extension of the back body of the diaper cover 11, a strip of raised cloth 15a is provided in the immediate vicinity inwardly from each Velcro fastener 15b such as to be parallel thereto.

Retaining straps 17 are attached to the inside of the front body of the diaper cover 11. The diaper body and the water-absorbing pad 1 secured therein which will later be described is held between the straps and the diaper cover. The retaining straps 17 may be made of rubber or cloth. The provision of such retaining straps 17 allows the diaper to be fitted to the wearer with the diaper body tightly held to cover 11, making the diaper easy to wear.

The retaining straps 17 are not necessarily attached obliquely as illustrated in FIG. 3, and may be attached in any manner provided that they can hold the diaper body to the cover. For example, the straps are affixed laterally.

Reference numeral 12 denotes an underlay sewed onto the inside of the back body of the diaper cover 11, whereby, if the excrement such as urine of a person lying on his back is leaked out of the diaper body, it can be absorbed. When washing diapers 10, the diaper body tends to be stretched by, for example, being entangled with other diaper bodies, in which case the underlay 12 serves also as stay cloth for reinforcement.

The diaper body is composed of an water-absorbing pad fixing cloth 13 (diaper sheet) and a backflow prevention sheet 14 (diaper sheet) put one on the other. One longitudinal end thereof is, using a Velcro fastener or the like, detachably attached to the cover such as to almost overlap with the lower edge section of the underlay 12.

The backflow prevention sheet 14 is fixed by one longitudinal end to the water-absorbing pad fixing cloth 13, and the other end can be lifted up from the water-absorbing pad fixing cloth 13.

The material of the water-absorbing pad fixing cloth 13 is the same as or different from that of the underlay 12, and cotton or the like is employed.

The backflow prevention sheet 14 is constituted of a base material 14a, such as three-dimensional mesh fabric or a water absorptive quick-dry material, and a cloth 14b sewed thereon. Due to the properties of the base material 14a, moisture can easily permeate through the backflow prevention sheet 14 from its surface-side (the surface which is brought into contact with the wearer's skin) to the back surface-side, but the sheet hardly allows moisture to permeate from the back surface-side to the surface-side. That is, the sheet 14 has such a property as to block the backflow of a fluid.

When wearing the diaper 10 the structure of which is such as was described above, firstly, the diaper body is integrally attached to the diaper cover 11. Then, the water-absorbing pad 1 is interposed between the water-absorbing pad fixing cloth 13 and the backflow prevention sheet 14 of the diaper body. Further, the free end of the diaper body (and water-absorbing pad 1) is inserted between the retaining straps 17 and the diaper cover 11 thereby to prevent the diaper body (and water-absorbing pad 1) from being dislocated from its proper position relative to the diaper cover 11.

Utilizing the Velcro fasteners 15b described above, the diaper is then fitted to the wearer. Since the diaper body (and water-absorbing pad 1) has been tightly secured to the diaper cover 11, as compared to a conventional diaper which is susceptible to the dislocation of the diaper body and the cover, the diaper of the present invention is easy to wear.

As compared to a diaper using cloth diapers only, in the case of the diaper 10 held to the wearer, the materials of the diaper body can be thinner and smaller in size, for the water-absorbing pad 1 secured therein has a sufficient absorbency and water-retaining capacity. Moreover, as compared to a conventional diaper which is used together with three cloth diapers, the diaper 10 of the present embodiment is lighter, meaning ease of handling for the carer who helps the user to wear the diaper 10 and allowing for smooth motion of the wearer during his/her rehabilitation.

If the wearer of the diaper 10 excretes urine or others, moisture permeates through the backflow prevention sheet 14 and reaches the water-absorbing pad 1. The moisture reached the water-absorbing pad 1 is absorbed by the water-absorbing polymer 3 via or while dissolving the water soluble paper 2.

Even if the water soluble paper 2 is dissolved, the risk of leakage of the water-absorbing polymer 3 out of the diaper body is extremely low, for the water-absorbing polymer 3 quickly absorbs water and swells to gel and the water-absorbing polymer 3 lies between the water-absorbing pad fixing cloth 13 and the backflow prevention sheet 14. Moreover, from the viewpoint of complete dispersion, dissolution or melting, or breaking of the crosslinks of the water-absorbing polymer 3 upon washing, dissolution of the water soluble sheet 2 is rather favorable than not.

Owing to the above-described property of the backflow prevention sheet 14, moisture once passed through the backflow prevention sheet 14 hardly flows back to the skin-side, alleviating unpleasantness the wearer feels or preventing skin-related troubles.

The used diaper 10 is wholly washable without removing the water-absorbing pad 1 therefrom every time, i.e., the diaper 10 is washable with the water-absorbing pad 1 interposed between the water-absorbing pad fixing cloth 13 and the backflow prevention sheet 14. It is also possible to wash, after the diaper body with the water-absorbing pad 1 secured therein has been removed from the cover 11, the diaper body and the cover separately.

As washing water (or rinsing water), an electrolytic aqueous solution, prepared from water (e.g., tapped water) and a suitable amount of salt, magnesium hydroxide, sodium hypochlorite, or calcium chloride dissolved therein, and a detergent are used. A detergent previously mixed with a suitable amount of an electrolytic substance may be employed. Moreover, a chemical, such as hypochlorous acid, may be added to an electrolytic aqueous solution in which salt or the like has been dissolved. The above-described electrolytic aqueous solution may be used for rinsing the diaper washed with a detergent.

By washing the diaper with an electrolytic aqueous solution, the water soluble paper 2 and the water-absorbing polymer 3 are dispersed, dissolved or melted, or the crosslinks of the water-absorbing polymer 3 are broken, leaving no garbage (non-flammable garbage) behind. Since the water-absorbing pad fixing cloth 13 and the backflow prevention sheet 14 each have a free end, washing water beats against both sides of the water-absorbing pad fixing cloth 13 or the backflow prevention sheet 14, effectively washing stains away.

When washing the diaper cover 11, as indicated by the arrows in FIG. 3, the extensions provided with the Velcro fasteners 15b are folded to adhere them to the raised cloth strips 15a thereby to prevent waste or others from clinging to the fasteners 15b upon washing.

By separately washing the diaper body and the diaper cover 11 as described above, not only it is possible to further prevent waste from sticking to the fasteners 15b, but also the risk of the cover 11 being contaminated with the dirt of the diaper body is eliminated.

Contaminated washing water can be discharged after having been subjected to ordinary sewage treatment (e.g., coagulation sedimentation or coagulation floatation treatment) at a waste water disposal plant to remove impurities to a level lower than the reference value set by the nation/prefecture/local authority or the public health center. Even in the case where the washing water is discharged into sewers, purification to a level lower than the reference value set by the nation or other authorities will be sufficient.

The diaper 10 thus washed and dried becomes reusable by sandwiching a new water-absorbing pad 1 between the sheets constituting the diaper body. However, if the diaper body is no longer usable because of stains that cannot be washed away or by being damaged, the diaper body detachable from the cover 11 is replaced with a new one, and only the diaper cover 11 is used again.

In the present embodiment, the case where only one longitudinal end with respect to the water-absorbing pad fixing cloth 13 of the backflow prevention sheet 14 is fixed and the other end can be lifted up from the water-absorbing pad fixing cloth 13 has been described thus far, but the backflow prevention sheet 14 may be sewed onto the water-absorbing pad prevention cloth 13 in the form of a pouch provided that the insertion of the water-absorbing pad 1 is not hampered.

Moreover, in the present embodiment, the water-absorbing pad 1 is interposed between the water-absorbing pad fixing cloth 13 and the backflow prevention sheet 14, but the pad 1 may be sandwiched by two cloth diapers.

Furthermore, in the present embodiment, the diaper body is detachable from the diaper cover 11, but it may be integrally attached to the diaper cover.

Second Embodiment

Figure 5:
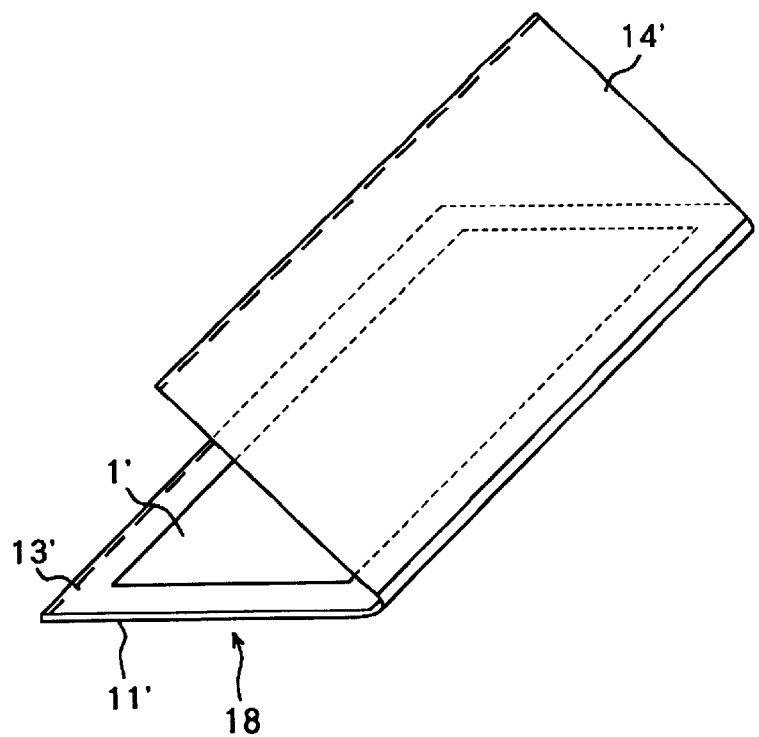
FIG. 5 is a schematic view of a urine-receiving pad which is a second embodiment of the present invention.
Figure 6:
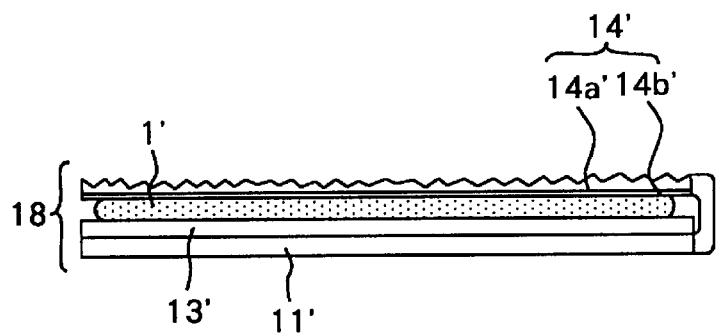
FIG. 6 is a cross-sectional view of the urine-receiving pad.

Illustrated in FIG. 5 and FIG. 6 is a urine-receiving pad (water-absorbing product) which is the second embodiment of the present invention.

The urine-receiving pad 18 is composed of an water-absorbing pad fixing cloth (sheet) 13' as a cover cloth, a backflow prevention sheet (sheet) 14', an water-absorbing pad 1' interposed therebetween, and a waterproof sheet 11' laid under the water-absorbing pad fixing cloth 13'.

The water-absorbing pad 1', water-absorbing pad fixing cloth 13', and backflow prevention sheet 14' are the same as the water-absorbing pad 1, water-absorbing pad fixing cloth 13, and backflow prevention sheet 14 described in connection with the first embodiment, respectively. However, these components are, as compared with those employed in the first embodiment, approximately half in size. The waterproof sheet 11' is made from the same material as that of the diaper cover 11 of the first embodiment or a material having similar properties. The size of the waterproof sheet 11' is almost the same as or slightly larger than that of the water-absorbing pad fixing cloth 13'.

The urine-receiving pad 18 having such structure is mounted on, for example, the diaper body (water-absorbing pad fixing cloth 13 and backflow prevention sheet 14) of the diaper 10 described in connection with the first embodiment or on a cloth diaper, i.e., on the side next to the wearer's skin.

When the water-absorbing pad 18 is fitted to a male, the pad is preferred to be mounted such as to take up a position off the center of the diaper body in the direction of the front body. If the wearer is a woman, the pad is preferred to be mounted such as to take up a position off the center of the diaper body in the direction of the back body.

In the case where the wearer excreted only urine, due to the absorbency of the urine-receiving pad 18, the backflow preventing function of the backflow prevention sheet 14', and the waterproofness of the waterproof sheet 11', the diaper body hardly gets wet with urine, so what is necessary is to change only the urine-receiving pad 18. Accordingly, as compared with the case where the diaper 10 is wholly replaced with a new one, so called "change of diaper" is made easier.

With the water-absorbing pad 1' secured within the urine-receiving pad 18, the pad 18 is washed in the manner similar to that described in connection with the first embodiment. Since the water-absorbing pad 18 is much smaller than the diaper 10, it is possible to wash a large number of pads at one time.

Since the number of components is small and it is compact for an water-absorbing product, cost reductions can be realized.

As shown by long broken lines in FIG. 5, the free edges of the water-absorbing pad fixing cloth 13' and the backflow prevention sheet 14' may be individually stitched with threads different in color from the sheet materials. With the color stitches along the free edges of the water-absorbing pad fixing cloth 13' and the backflow prevention sheet 14' as marks, the used urine-receiving pad 18 is taken out of the diaper with its color-stitched side up, whereby the risk of the water-absorbing polymer spilling out of the pad is reduced.

Third Embodiment

The first and second embodiments are diapers using the water-absorbing pads 1 and 1', but an water-absorbing pad of the same structure can be utilized for incontinence panties, towels, and products required to have a high absorbency other than diapers.

Figure 7:
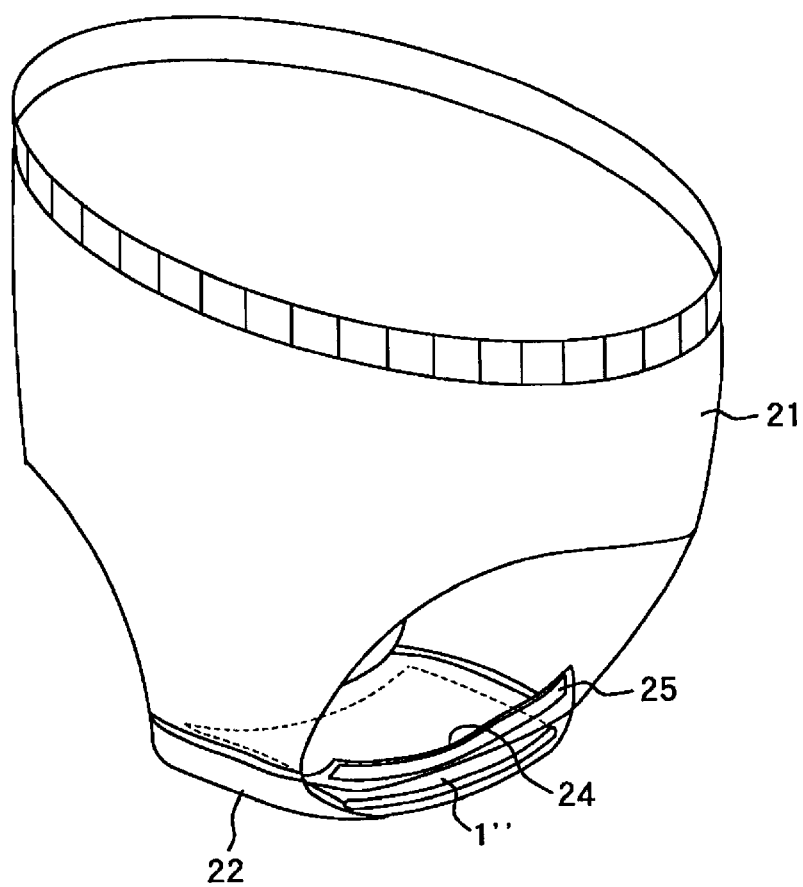
FIG. 7 is a perspective view of an incontinent panty which is a third embodiment of the present invention.

An example of the incontinence panty is shown in FIG. 7. In this figure, indicated by reference numerals 21 and 22 are the body of a panty and a crotch portion, respectively.

The crotch portion 22 is in the form of a pouch constituted of two sheets in layered relation (inner side: backflow prevention sheet material, outer side: cotton or waterproof sheet material). A flap 24 provided at the side opening is fastened with a Velcro fastener 24.

After an water-absorbing pad 1" (e.g., an water-absorbing pad having the same structure as that of the second embodiment) sized to fit the crotch portion 22 has been inserted from the side opening into the crotch portion 22, the flap 24 is closed.

Owing to the absorbency and water-retaining function of the water-absorbing pad 1", the incontinence panty having such structure also can absorb urine or other fluids sufficiently. The panty, after its use, is washed in the same manner as in the case of the diaper 10 to be used again. Thus, no garbage is generated.

The first to third embodiments described above are the cases in which an water-absorbing pad constituted of a water soluble sheet in the form of an envelope and an water-absorbing polymer sealed therein is used, but the pad may be formed by incorporating a water soluble material having the same properties as those of the water soluble paper with the water-absorbing polymer or inserting the polymer thereinto. In any case, the water-absorbing pad need only be such that the water soluble component is dissolved and the water-absorbing polymer is dispersed, dissolved or melted, or the crosslinks of which are broken in an electrolytic aqueous solution.

In the first embodiment, the diaper 10 is washed with washing water in which an electrolytic substance such as salt has been dissolved, but the electrolytic substance may be impregnated into the water-absorbing pad. For example, the electrolytic substance may be mixed into the water-absorbing polymer. The corners of the water soluble paper 2 may be impregnated with the electrolytic substance. Alternatively, the electrolytic substance, wrapped up with water soluble paper other than the water soluble paper 2, may be put in a pouch of the water soluble paper 2. Moreover, the electrolytic substance or electrolytic aqueous solution may be previously mixed into a water soluble adhesive for adhering the water soluble paper 2 of the pad 1. By doing so, the electrolytic substance incorporated into the water-absorbing pad or into the adhesive is dissolved in washing water (water) upon washing, which consequently eliminates the necessity for dissolving an electrolytic substance in washing water every time the user washes the diaper, leading to the convenience of washing.

Fourth Embodiment

Figure 8:
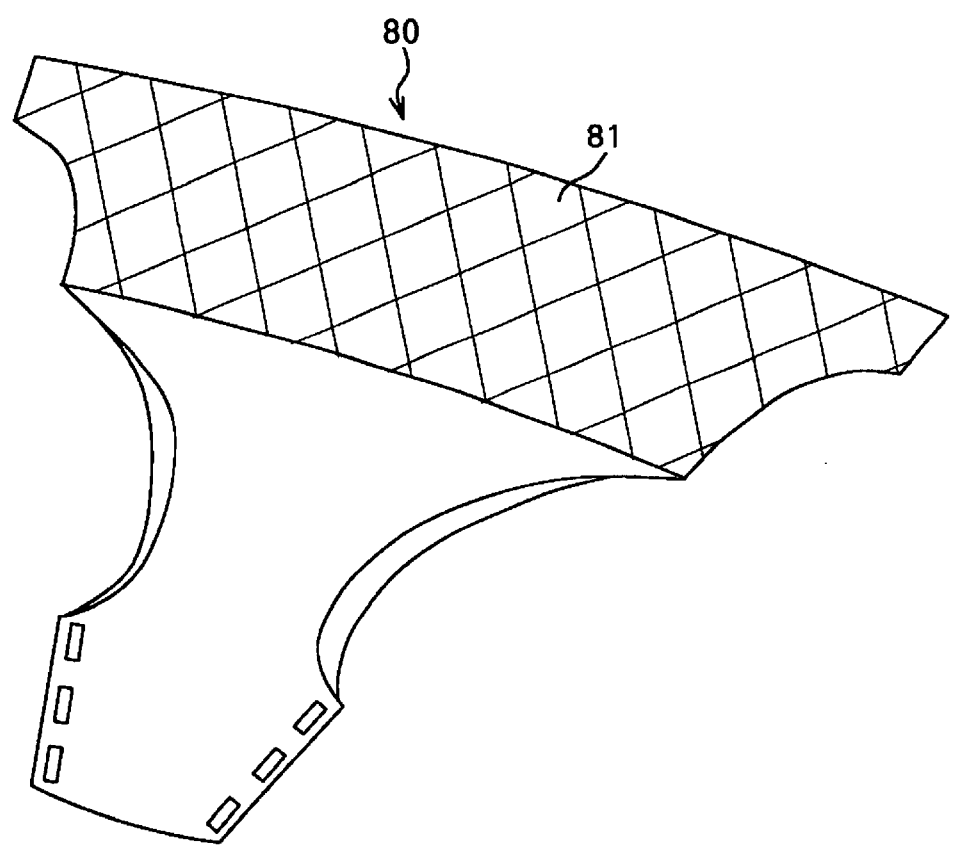
FIG. 8 is a perspective view of a diaper cover which is a fourth embodiment of the present invention.

FIG. 8 shows a diaper cover for a diaper being the fourth embodiment of the present invention. A slippage prevention cloth 81 is attached to the inside of the back body of the diaper cover whereby to prevent the slippage of a cloth diaper (with an water-absorbing pad secured therein) which is placed on the cover 80.

Fifth Embodiment

Figure 9:
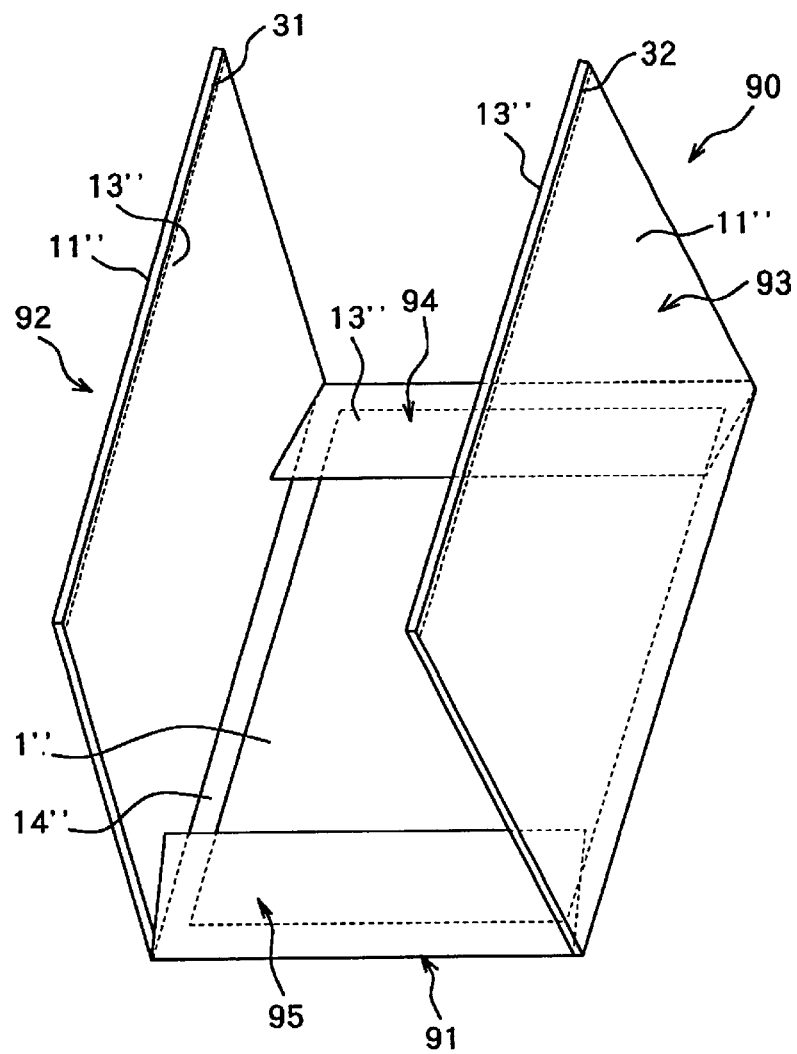
FIG. 9 is a schematic view of a urine-receiving pad which is a fifth embodiment of the present invention.
Figure 9:
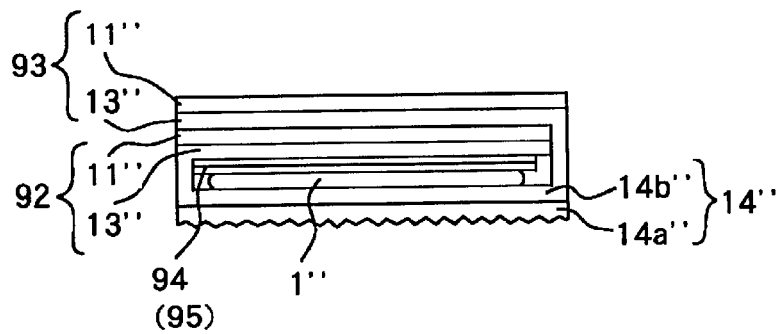

FIG. 9 is a schematic and cross-sectional view of an urine-receiving pad (water-absorbing product) being the fifth embodiment of the present invention.

A urine-receiving pad 90 shown in FIG. 9 is composed of an water-absorbing pad 1" formed in the same manner as in the case of each embodiment described above and enclosed in a folded covering sheet 91.

The covering sheet 91 has a pad mount section constituted of a base material 14a" such as a three-dimensional mesh fabric or an water-absorbing quick-dry material, and a cloth 14b" sewed thereon. A pair of flaps 92 and 93 are provided on both sides of the pad mount section, the flaps being constituted of an water-absorbing pat fixing cloth 13" (may be integrally formed with the cloth 14b") and a waterproof sheet 11" sewed together. A pair of small flaps 94 and 95 made of the water-absorbing pad fixing cloth 13" are provided at the front and rear of the pad mount section. With the water-absorbing pad 1" placed on the pad mount section, firstly, the small flaps 94 and 95 of the covering sheet 91 are folded. Then, the flaps 92 and 93 are alternately folded.

Color threads 31 and 32 different in color from the sheet materials are used to sew the edges of the flaps 92 and 93.

The color thread 31 (or 32) is exposed on the openable side of the folded cover sheet 91.

By detaching the used urine-receiving pad 90 with the side stitched with the color thread 31 (or 32) (i.e., the edge with marks) up, the water-absorbing polymer is prevented from spilling out of the pad 90.

Sixth Embodiment

Figure 10:
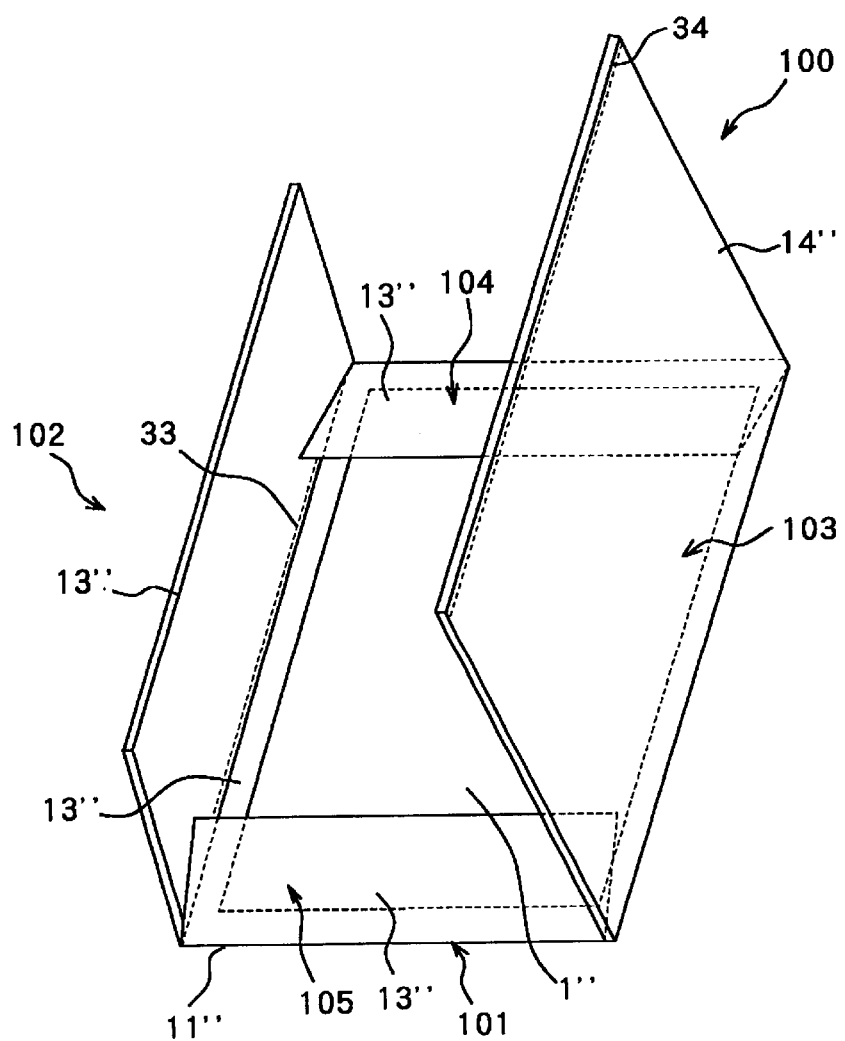
FIG. 10 is a schematic view of a urine-receiving pad which is a sixth embodiment of the present invention.
Figure 10:
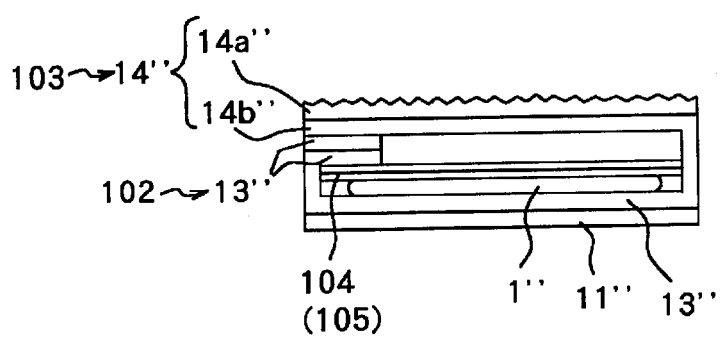

FIG. 10 is a schematic and sectional view of an urine-receiving pad (water-absorbing product) which is the sixth embodiment of the present invention.

A urine-receiving pad 100 shown in FIG. 10 is composed of an water-absorbing pad 1" made in the same manner as in the case of each embodiment, and a covering sheet 101. The pad is placed inside the folded covering sheet.

The covering sheet 101 has a pad mount section constituted of a waterproof sheet 11" and an water-absorbing pad fixing cloth 13" sewed thereon, a pair of flaps 102 and 103 provided on both sides of the pad mount section, and a pair of small flaps 104 and 105 provided at the front and rear of the pad mount section.

Between the left and right flaps 102 and 103, the larger one, i.e., the flap 103 (having an area almost the same as that of the pad mount section) is constituted of a base material 14a" such as a three-dimensional fabric or an water-absorbing quick-dry material, and a cloth 14b" (may be formed integrally with the water-absorbing pad fixing cloth 13") sewed thereon.

With the water-absorbing pad 1" placed on the pad mount section, firstly, the front and rear flaps 104 and 105 of the covering sheet 101 are folded. Secondly, the smaller flap 102 and then the flap 103 are folded.

The fold line of the flap 102 is stitched with a color thread 33 different in color from the covering sheet, and the free edge of the flap 103 is stitched with a color thread 34 different in color from the covering sheet.

The color threads 33 and 34 are exposed on the openable side of the folded covering sheet 101. By detaching the used urine-receiving pad 100 with the edges stitched with the color threads 33 and 34 (i.e., with marks) up, the water-absorbing polymer is prevented from spilling out of the pad 100.

In the fifth and sixth embodiments described above, the waterproof sheet 11' is made of the same material as that of the diaper cover described in connection with the first and second embodiments, or of a material having similar properties.

How the covering sheet is folded, the size of each flap, and the way of marking described in connection with the fifth and sixth embodiments are for purposes of illustration only and may be suitably modified.

Seventh Embodiment

Figure 11:
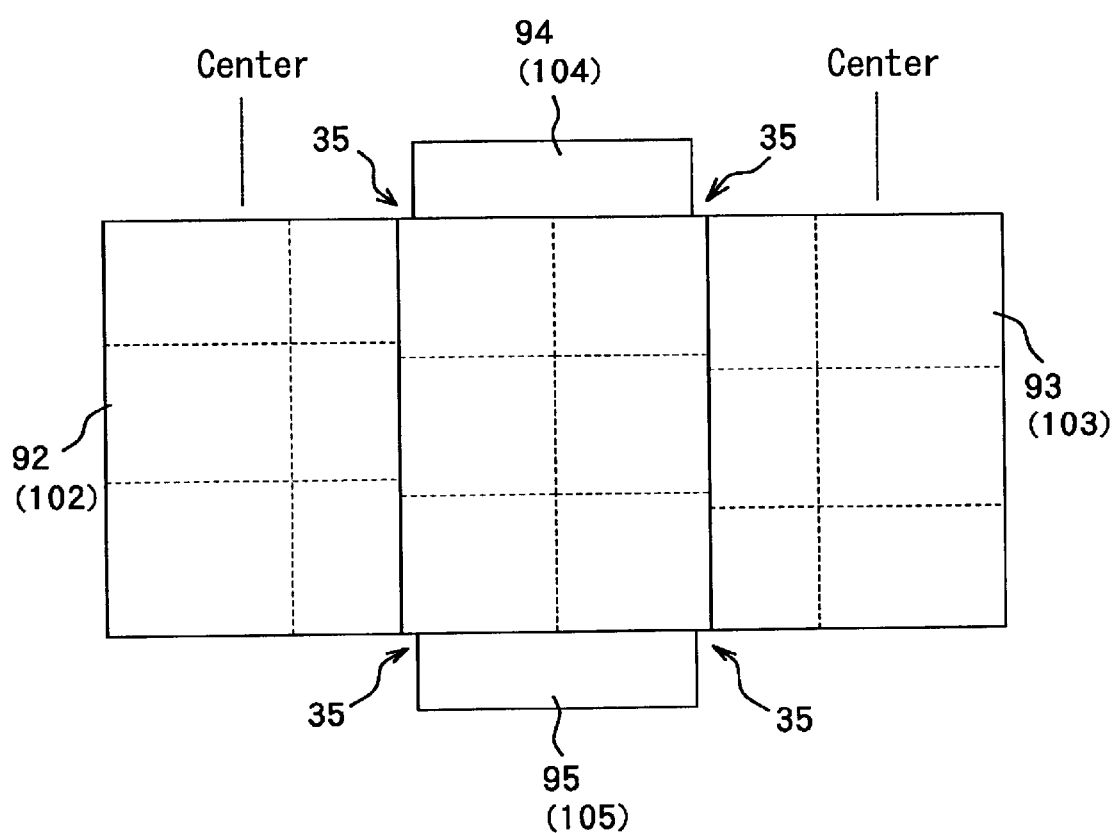
FIG. 11 is a developed view of the covering sheet for a urine-receiving pad which is a seventh embodiment of the present invention.

FIG. 11 shows another embodiment of the covering sheet for the urine-receiving sheet of the fifth or sixth embodiment.

In the fifth and sixth embodiments, if a set of the base material 14a" such as a three-dimensional mesh fabric or an water-absorbing quick-dry material and the cloth 14b", and a set of the water-absorbing pad fixing cloth 13" and the waterproof sheet 11" are individually sewed only along their edges, when washed, these are spread out and may come apart at their seams or, due to the difference in the degree of shrinkage of the materials, they may become slack.

For preventing such rips or slack, as indicated by dotted lines in FIG. 11, in regions inward from the edges of the two-layered sections (the pad mount section, the flaps 92 and 93 (102, 103)), these two sheets are sewed together (for example, one line of stitches laterally, two lines of stitches longitudinally), whereby rips or slack is effectively prevented.

However, if the positions of the seams in the pad mount section and the left and right flaps 92 and 93 (102, 103) coincide with each other when the covering sheet is folded, water (e.g., urine) could seep from the seams. So, in the present embodiment, the seams in the pad mount section and the left and right flaps 92 and 93 (102, 103) are misaligned so as not to overlap when the cover is folded.

To be concrete, not only are the heights of the two seams in the left flap 92 (102) different from those of the seams in the right flap 93 (103), the longitudinal seams in the left and right flaps 92 and 93 (102, 103) are positioned off the respective centers of the flaps in the direction of the pad mount section.

By doing so, water is prevented from seeping from the seams. The positions and the number of seams shown in FIG. 11 are for purposes of illustration only, and they may be suitably selected.

In the covering sheet of the present embodiment, as indicated by the reference numeral 35, the widths of the front and rear flaps 94 and 95 (104, 105) are set at values smaller than the width of the pad mount section.

If the widths of the flaps 94 and 95 (104, 105) and that of the pad mount section are the same, when the left and right flaps 92 and 93 (102, 103) are folded after the front and rear flaps 94 and 95 (104, 105) have been folded, cares must be paid so that the flaps are not creased, and therefore the cover will be difficult to fold.

In addition, if the widths of the flaps and the pad mount section are the same, depending on the degree of shrinkage after washing, the sides of the front and rear flaps 94 and 95 (104, 105) opposite to their other sides connected to the pad mount section will be longer than the width of the pad mount section. Thereby, when the cover is folded, it may result in wrinkles and slack or folds.

Such problem is solved by making the width of each of the front and rear flaps 94 and 95 (104, 105) shorter than that of the pad mount section, and the cover will be easily foldable.

The urine-receiving pads have been described thus far as the fifth to seventh embodiments, but their structure is also applicable to diapers. A diaper having the same structure as that of the urine-receiving pad may be used detachably from the diaper cover.

As described above, when interposed between sheets of cloth or other materials that are employed for water-absorbing products represented by diapers, since the water-absorbing pad of the present invention ensures sufficient absorbency and water-retaining capacity as an water-absorbing product. Thus, the materials of the product themselves are not required to have a high absorbency, and thin and light fabrics can be employed. Therefore, it is made possible to reduce the weight of the entire product.

A conventional cloth diaper is required to be wrapped around the waist of the wearer thereby to prevent the leakage of urine or other fluids, but the use of the diaper of the present invention eliminates the necessity of wrapping a cloth diaper in such manner, making diaper change easier.

Moreover, by using a sheet of such a material as to allow moisture (e.g., urine) to easily permeate from its surface-side to the water-absorbing pad-side but hardly allows the reverse as at least one of the sheets between which the water-absorbing pad is interposed (e.g., the skin-side sheet), the moisture absorbed into the pad is prevented from flowing back, releasing the wearer from unpleasantness or skin troubles.

By washing a used water-absorbing product with an electrolytic aqueous solution such as a salt solution in an ordinary manner with its water-absorbing pad incorporated therein, the water-absorbing pad is dissolved, leaving no garbage behind. This not only enables the water used for washing to be discharged without any special sewage treatment but makes it possible to reuse the water-absorbing product.

By making a set of diaper sheets between which the water-absorbing pad is interposed detachable from the diaper cover, not only does the diaper become easier to wear with the set of diaper sheets (and the water-absorbing pad interposed therebetween) integrally attached to the cover, but also even if the diaper sheets are stained or damaged to uselessness, it is possible to reuse the diaper cover together with a new set of diaper sheets.

The necessity for adding an electrolytic substance to washing water every time the water-absorbing product is washed can be eliminated by impregnating the water-absorbing pad with an electrolytic substance, incorporating an electrolytic substance or electrolytic aqueous solution into a glue or adhesive to be used for gluing the water soluble sheet, or using a detergent previously mixed with a suitable amount of an electrolytic substance.

What is claimed is:

1. A water-absorbing pad comprising:
    a water-absorbing polymer having a characteristic such that the polymer is dispersed or dissolved in an electrolytic aqueous solution; and
    a water soluble material in a flat sheet form for wrapping the polymer to retain the same therein so that when the water-absorbing pad is held in a sufficient amount of the electrolytic aqueous solution, the water-absorbing pad is quickly dispersed or dissolved in the aqueous solution.

2. The water-absorbing pad according to claim 1, wherein said water-absorbing polymer has crosslinks therein, said crosslinks being broken in the electrolytic aqueous solution.

3. The water-absorbing pad according to claim 2, wherein said water-absorbing polymer is a crosslinked polyacrylate resin or a crosslinked polystarch acrylate resin.

4. The water-absorbing pad according to claim 2, wherein said water soluble sheet is a sheet of water soluble paper.

5. The water-absorbing pad according to claim 2, wherein said water soluble sheet is a water soluble non-woven fabric.

6. The water-absorbing pad according to claim 1, further comprising an electrolytic substance therein.

7. The water-absorbing pad according to claim 1, further comprising an adhesive for gluing said water soluble sheet and an electrolytic substance mixed in the adhesive.

8. A water-absorbing product, comprising the water-absorbing pad as recited in claim 1 and sheets, the water-absorbing pad being interposed between the sheets.

9. The water-absorbing product according to claim 8, wherein at least one of the sheets between which said water-absorbing pad is interposed is made of a material to allow moisture to easily permeate from its surface-side to a water-absorbing pad-side but prevent the moisture to permeate from the water-absorbing pad-side to the surface-side.

10. The water-absorbing product according to claim 9, further comprising a waterproof sheet attached to an outside of the other of the sheets between which said water-absorbing pad is interposed.

11. The water-absorbing product according to claim 8, wherein said sheets for enclosing the water-absorbing pad have an openable side with a mark.

12. The water-absorbing product according to claim 8, wherein said sheets for wrapping the water-absorbing pad includes overlapped portions constituted of a set of at least two sheets sewed together by seams, and said seams are made so as not to overlap with each other when said sheets are folded.

13. The water-absorbing product according to claim 8, wherein said sheets for wrapping the water-absorbing pad includes a pad mount section on which said water-absorbing pad is placed, and four flaps around the pad mount section, a pair of flaps in the four flaps being made shorter in width than said pad mount section.

14. A diaper comprising the water-absorbing product as recited in claim 8 and diaper sheets made of diaper materials which are used together with the water-absorbing product.

15. A diaper comprising the water-absorbing pad as recited in claim 1 and sheets of diaper materials covering the water-absorbing pad.

16. The diaper according to claim 15, wherein one of the sheets which partly covers the water-absorbing pad and is brought into contact with a skin is made of a material as to allow moisture to easily permeate from its surface-side to a water-absorbing pad-side but prevent moisture to permeate from the water-absorbing pad-side to the surface-side.

17. The diaper according to claim 14, wherein said diaper sheets for wrapping the water-absorbing pad include an openable side with a mark.

18. The diaper according to claim 14, wherein said diaper sheets for wrapping the water-absorbing pad include overlapped portions constituted of a set of at least two sheet portions sewed together by seams, and said seams are made so as not to overlap with each other when said diaper sheets are folded.

19. The diaper according to claim 14, wherein said diaper sheets for wrapping the water-absorbing pad include a pad mount section on which said water-absorbing pad is placed, and four flaps around the pad mount section, a pair of flaps in the four flaps being made shorter in width than said pad mount section.

20. The diaper according to claim 14, further comprising a diaper cover, said diaper sheets being detachable from the diaper cover.

21. The diaper according to claim 14, further comprising a diaper cover, said diaper sheets being integrally attached to the diaper cover.

22. The diaper according to claim 20, further comprising a fastener attached to said diaper cover to hold the diaper cover in a shape of a panty, and a strip of raised cloth which adheres to the fastener provided in an immediate vicinity of the fastener, a fastener-provided portion of the diaper cover unfolded from the shape of a panty being folded to adhere the fastener to the strip of raised cloth.

23. The diaper according to claim 20, further comprising a piece of fabric to prevent said set of diaper sheets from being dislocated, said piece of fabric being attached to an inside of said diaper cover.

24. A method for washing a water-absorbing product composed of a water-absorbing pad formed of a water-absorbing polymer which is dispersed or dissolved in an electrolytic aqueous solution, and sheets between which the pad is interposed, said method comprising the step of washing the water-absorbing product with the water-absorbing pad interposed between the sheets by the electrolytic aqueous solution so that the sheets with the water-absorbing pad is quickly dispersed or dissolved in the aqueous solution.

25. The method for washing a water-absorbing product according to claim 24, wherein the water-absorbing product is washed with a detergent previously mixed with an electrolytic substance.

26. A method for washing a diaper composed of a water-absorbing pad formed of a water-absorbing polymer which is dispersed or dissolved in an electrolytic aqueous solution, and sheets between which the pad is interposed, said method comprising the step of washing the diaper with the water-absorbing pad interposed between the diaper sheets by the electrolytic aqueous solution so that the sheets with the water-absorbing pad is quickly dispersed or dissolved in the aqueous solution.

27. The method for washing a diaper according to claim 26, wherein the diaper is washed with a detergent previously mixed with the electrolytic substance.

28. The method for washing a diaper according to claim 26, wherein the diaper has a diaper cover to which said set of diaper sheets is attached, and the diaper is washed with the set of diaper sheets between which said water-absorbing pad is interposed.

29. The method for washing a diaper according to claim 28, wherein said diaper cover includes a fastener attached to said diaper cover to hold the diaper in a shape of a panty, and a strip of raised cloth provided in an immediate vicinity of the fastener, the diaper in a condition that a fastener-provided portion of the diaper cover unfolded from the shape of a panty is folded to adhere the fastener to the strip of raised cloth being washed.

* * * * *